(12) United States Patent
Ardö et al.

(10) Patent No.: US 7,082,370 B2
(45) Date of Patent: Jul. 25, 2006

(54) LOCALIZATION OF A POINT SOURCE OF A VISUALIZED GAS LEAK

(75) Inventors: Björn Ardö, Lund (SE); Tomas Christiansson, Lund (SE); Jonas Sandsten, Lund (SE)

(73) Assignee: Gasoptics Sweden AB, Lund (SE)

( * ) Notice: Subject to any disclaimer, the term of this patent is extended or adjusted under 35 U.S.C. 154(b) by 0 days.

(21) Appl. No.: 10/887,136

(22) Filed: Jul. 8, 2004

(65) Prior Publication Data

US 2005/0049804 A1 Mar. 3, 2005

(30) Foreign Application Priority Data

Sep. 2, 2003 (SE) .................................. 0302336

(51) Int. Cl.
*G01B 5/00* (2006.01)
*G06F 19/00* (2006.01)

(52) U.S. Cl. ......................................... 702/51; 702/36

(58) Field of Classification Search ................. 702/34, 702/35, 36, 50, 51, 58, 59, 79, 159; 73/40, 73/40.5 A, 40.5 R, 592; 33/1 CC, 303, 314

See application file for complete search history.

(56) References Cited

U.S. PATENT DOCUMENTS

| | | | |
|---|---|---|---|
| 5,205,173 A * | 4/1993 | Allen | 73/592 |
| 6,389,881 B1 * | 5/2002 | Yang et al. | 73/40.5 A |
| 6,446,491 B1 * | 9/2002 | Pompa et al. | 73/40.5 R |

* cited by examiner

*Primary Examiner*—Bryan Bui
(74) *Attorney, Agent, or Firm*—Ladas & Parry LLP (57) ABSTRACT

Automated localization of a point source of a visualized gas leak, by searching in a corner response function $crf(x^*,y^*,\tau)$, calculated based on a number of frames of the gas leak, for maximum values in the $(x^*,y^*)$ variables that are stable over the time variable $\tau$. Considering a point $(x^*,y^*)$ as the point source if the corner response function $crf(x^*,y^*,\tau)$ has a maximum value in the point $(x^*,y^*)$ and the point $(x^*,y^*)$ is temporally stable.

42 Claims, 4 Drawing Sheets

LOCALIZATION OF A POINT SOURCE OF A VISUALIZED GAS LEAK

FIELD OF THE INVENTION

The present invention refers to localization of a point source of a visualized gas leak. Especially the present invention refers to automatic localization of a point source of a visualized gas leak using for instance gas correlation technique.

BACKGROUND OF THE INVENTION

When using visualization systems to monitor leaks in a gas processing plant, there is a need to quickly and automatically locate the origin of the leak in the gas processing plant in order to take appropriate counter-actions. If the leak is a security risk it is favorable to shut down the production automatically without human intervention. If the location of the point source of the leak is not known then the entire plant has to be shut down to control the leak. Clearly, it is of economical interest to only shut down the affected subsystems.

If a shutdown decision should be taken by an operator it is useful to translate the optical information in the gas image to schematic information in an electronic plant overview plan.

It is of great importance for both safety and environmental reasons to detect and quantify a gas leak and determine its mass flux. Most techniques to determine the mass flux utilizes prior knowledge of where the point source is located. Sometimes, like in the lidar (Light Detection And Ranging) case, it is enough to know that the point is to the left or right of the scene of interest but sometimes the exact location must be known. The position of the leak in the gas image is required for automatic determination of the mass flux.

The method used today to locate the origin of a leak visualized with gas visualization techniques is to rely on the judgement of the operator. With the gas information mixed with a visual image the human brain has little problem in determining the origin of the leak.

A method used today to find a leak without gas visualization techniques is to use point detectors. To locate the origin of the leakage, it is required to walk around the plant with gas point detectors or to look at secondary effects from the leak such as the cooling of the pipe when the gas pressure drops.

Lidar technology can be used to determine the existence of leaks and the total mass flux of these. Locating the origins of these leaks can typically take weeks or months after the measurement. Lidar measurements require large and heavy instruments and are normally only performed once every second year if at all employed.

SUMMARY OF THE INVENTION

An object of the present invention is thus to improve the localization of a point source of a visualized gas leak. An aim of the object is to provide automatic localization of a point source of a visualized gas leak, using for instance gas correlation technique, requiring a minimum of human intervention.

Another object of the present invention is to provide information that facilitates the decision-making to an operator of a plant or refinery. Such information can for example be the location of a point source of a visualized gas leak in relation to the physical construction of the plant, whereby the operator more easily can decide whether to shut down a subsystem of the plant or the entire plant in order to take care of the gas leak.

In order to fulfill the above-mentioned objects and aims among others, the present invention refers to a method, an equipment, a monitoring system and a computer program product according to the independent claims claims invention. Preferred embodiments of the invention are defined in the dependent claims.

The drawings and detailed description of the invention show and essentially describe only preferred embodiments of the invention. As will be recognized by a skilled person in the art, the invention can relate to other embodiments, and its several details may be subject to modification in various respects, all without departing from the inventive concept. Accordingly, the drawings and detailed description are to be regarded as having an illustrative nature and are not intended to restrict the scope of the present invention.

BRIEF DESCRIPTION OF THE DRAWINGS

The present invention will be described with reference to the accompanying drawings, in which.

DETAILED DESCRIPTION OF THE INVENTION

The invention thus refers to localization of one or several point sources of a visualized gas leak. Especially the present invention refers to automatic localization of one or several point sources of a visualized gas leak using for instance the gas correlation technique.

The present invention relies on a number of physical properties of gas leaks. The most important ones are the turbulent structure of the gas at different distances from the gas source and the fixed location in space of the gas source. The occurrence of a strong concentration gradient which features a corner-shaped behavior in the gas images at the source is also used.

The gas concentration distribution is a four-dimensional function in time and space. Gas visualization techniques project this function to a three-dimensional function by integrating along one of the space coordinates, or more precisely, integrating along the lines corresponding to the same point in the projective transform. In this description text, the three-dimensional function of the gas distribution is called g(x*,y*,t). The point sources are structures that show stability in all three coordinates. Here x and y refers to a coordinate system independent of the rotation and translation of the camera.

Generally, the present invention can be seen as a search in a corner response function crf(x*,y*,τ), calculated based on a number of frames of a gas leak, for maximum values in the (x*,y*) variables that do not move when altering the time τ variable, i.e. that are stable over time and considering a point (x*,y*) as a point source if the corner response function crf(x*,y*,τ) has a maximum value in the point (x*,y*) and the point (x*,y*) is temporally stable.

More specifically, the localization of the leak source according to an embodiment of the invention is accomplished by four main steps, namely 1) performing a temporal averaging by determining the partial integral in the time coordinate, i.e. calculating the temporal average of a number of frames of a taken set of gas images, 2) locating possible source points by calculating the corner response function (crf) of the temporally averaged image, 3) determining one or several local maximum points of the corner response function (crf) and considering said local maximum points as possible source points of leakage, and 4) determining the temporal stability of the possible sources. These four steps will be described in more detail below.

The first step in the inventive method in order to localize a point source of a visualized gas leak is to calculate the temporal average of a number of frames of a set of gas concentration images, which images have been taken in a time sequence by means of a device for imaging of gas distributions utilizing optical techniques. More specifically, the temporal average is taken of a number of frames around the frame in which the source is to be found. If the source is to be found in real time the average has to be taken of frames earlier in time. This temporal averaging is performed to attenuate the turbulent effects that appear far from the source and change a lot over time. The more stable structures close to the gas source are enhanced by this operation. This step is optional but enhances the performance.

Thus the first step is a temporal average and is performed by the partial integral in the time coordinate. The temporal average is called $f(x,y,\tau)$ and defined as $$f(x, y, \tau) = \frac{1}{t_0} \int_{\tau-t_0}^{\tau} g(x, y, t) \partial t.$$

Figure 1:
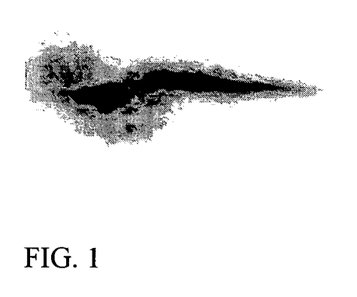
FIG. 1 shows an image of the temporal average of a number of frames.

The spatial areas far from the source with a lot of turbulence will be smoothed by the temporal averaging. FIG. 1 illustrates an example of the temporal average of a number of frames, in which figure the regions of the gas jet far away from the source are smoothed and the region close to the source retains its shape.

In the resulting temporal averaged image, with reduced turbulence, the gas source has a sharp corner like structure. The second step is to calculate the corner response function (crf). All the local maxima of the corner response function (crf) are considered as possible sources of gas leakage and are stored in a candidate list comprised in a storing means.

Thus, in the second step, the corner response function is calculated in the spatial directions in order to locate possible source points. This is performed by evaluating the singular covariation matrices of the spatial gradient of $f(x,y,\tau)$. This matrix is defined as m=aa* where a is defined as $$a = \begin{pmatrix} \frac{\partial f}{\partial x} \\ \frac{\partial f}{\partial y} \end{pmatrix}.$$

The spatial average of m(x,y,τ) is calculated as $$m^*(x^*, y^*, \tau) = \iint_{x,y \in N(x^*,y^*)} m(x, y, \tau) \partial x \partial y$$

where N(x*,y*) is a small area around the point (x*,y*). This spatial average could possibly be weighted by a factor depending on the distance from the point (x*,y*). The eigenvalues $(\lambda_1(x^*,y^*,\tau),\lambda_2(x^*,y^*,\tau))$ of m*(x*,y*,τ) are then calculated and the corner response function is defined as crf(x*,y*,τ)=c|$\lambda_1\lambda_2$|−|$\lambda_1^2+\lambda_2^2$| where c is a constant. The constant c can be calculated as (cf+1/cf) where cf is a positive number. Thus, the constant c is larger than or equal to 2. In an ideal case, an eigenvalue is 0 and another large at a non-corner, resulting in a negative corner response function. Further, in the ideal case, a corner has two equally large eigenvalues and then the corner response function will be larger, the larger the constant c is. However, in reality even moderate corners will be amplified by a large value of the constant c.

If the gradient does not change much then m*(x*,y*,τ) will be close to singular with one eigenvalue close to zero and the corner response function crf(x*,y*,τ) will be negative. If the gradient however does change a lot then the matrix will have two nonzero eigenvalues and with c chosen correctly, the corner response function crf(x*,y*,τ) will be large. The larger the gradient is, the larger the corner response function crf(x*,y*,τ) will be, so the corner response function crf(x*,y*,τ) will be large in areas where the temporal average $f(x,y,\tau)$ has a large gradient that is changing a lot.

To be able to detect possible gas sources without prior knowledge of the magnitude of the leak, the strongest corner feature is located in the third step. This is accomplished in that the candidate list is sorted by the corner response and the strongest candidate is found. The value of the located corner response is a dynamic measure of how large typical corner response values are in a particular case. A threshold based on the corner response value of the strongest candidate is used to remove possible sources having a too low corner response value, i.e. all candidates having a value lower than a factor times the strongest corner response are removed from the list.

Figure 2:
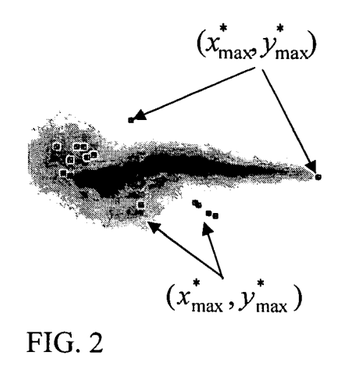
FIG. 2 shows the image of FIG. 1 with all the local maxima of the corner response function located.
Figure 3:
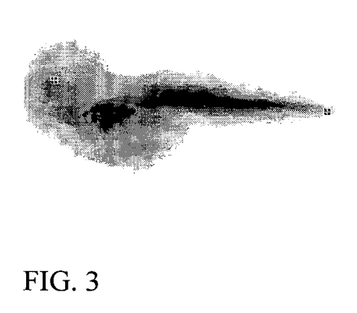
FIG. 3 shows the image of FIG. 2 with all points having a lower corner response than a factor times the largest one removed.

Thus, in the third step, all the spatial local maximum values of the corner response function crf(x*,y*,τ) are calculated for each value of the time τ. In this set of points the point $(x_{max}^*,y_{max}^*)$ with the largest value of the corner response function crf(x*,y*,τ) for each τ is found. FIG. 2 shows an image corresponding to the image of FIG. 1. However, in FIG. 2 all the local maxima of the corner response function are located and shown as several small black squares. A threshold based on the largest value of the corner response is used to remove points from the set. That is for each τ all points in the set with a corner response value less than $k \cdot crf(x_{max}^*, y_{max}^*, \tau)$ is removed. Here k is a constant between 0 and 1. The resulting image is shown in FIG. 3.

The constant k can be set in dependence of the number of possible sources one want to receive. If for example only one possible source is desirable, a high value of k should be chosen. On the contrary, a low value of k should be selected if all possible sources are to be found, even if one of the possible sources turns out to be false.

Figure 4:
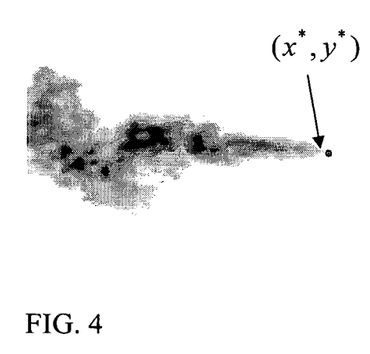
FIG. 4 shows the image of FIG. 3 with the all points not stable in time removed.

The fourth step in the procedure according to the invention is based on the fact that the leakage source does not move over time. The temporal stability of all the possible sources is investigated. This is done by examining the candidate list for possible sources a number of frames earlier having the very same location in space. If a point among the present possible sources is stable enough, i.e. the location does not vary or varies minimally, over time then it is considered as a leak source. Thus, a point that is stable in the time τ variable is a possible leak origin. For a point $(x_1^*, y_1^*)$ to be considered stable in τ at the time $\tau_1$ there has to exist at least one point in every set between $[\tau_1 - \Delta\tau, \tau_1]$ that belong to the open ball $B_r(x_1^*, y_1^*)$, where r is a constant distance, measured with some norm, for instance the $L_2$, $L_1$, or $L_\infty$ norm. The situation when only the points stable in time are saved is shown in FIG. 4. As seen from FIG. 4 only one point is found, i.e. the right-most point indicated as $(x^*, y^*)$, and this point is thus considered as the point source of the gas leak.

If the real time demand is reduced then the stability of the points over time can be investigated for following frames as well as prior frames, i.e. for frames taken at point of times after or before the frame in which the source is to be located.

If other a priori information is known, this information can be used to rank the points in the candidate list, comprising the found local maximum points, in another way. Such a priori information is for example the geometry of the plant.

Optionally, embodiments of the invention also comprise noise reduction. Concentration images of the gas leak may contain many different kinds of noise. Some of the noise may come from the detector, i.e. the optical equipment taking the images of the gas leak, and some from the measurement procedure itself. Before calculations are made on the images, as much as possible of the noise should preferably be removed. The removal of the noise can be done in different steps. The noise can for example be removed using a variable threshold, median filtering with morphological operations, Gaussian filtering and/or a Wiener filter.

The images can for example contain a cyclic noise that manifests itself as horizontal lines which moves up and down in the image. This noise is probably an artifact from the detector. Since this noise has nothing to do with the actual gas distribution it should be removed if possible.

The cyclic noise can be removed by analyzing the images in the Fourier plane and calculating the mean of the absolute value of the Fourier coefficients of a sequence of images. Clearly distinct spots at higher frequencies may exist both in images containing gas and images with just noise in them resulting from unwanted noise. In some images, the large concentration of frequencies at the vertical line through origin can specially be noted. These frequencies correspond to horizontal lines and this is the noise that should be eliminated.

To eliminate this noise, the frequencies where it exists can be located from the average of many images. The average of the absolute value in a slightly larger area around these frequencies was calculated for each frame. The noise frequencies can then be scaled to this value if they are larger than the mean. In this way the noise frequencies are only removed if they are present and dominant and a reasonable reconstruction level have been chosen. This is to make as little damage to the signal data as possible.

When noise exists in the images, the best thing would be, if possible, to locate the physical reason for the noise and eliminate it as close to the source as possible. This may mean to replace the detector.

The measurement procedures may rely on the fact that there is a temperature difference between the gas and the background. If these two have almost the same temperature then the value will be very noisy. Since an IR-image that has been gas filtered can be seen as a temperature image of the background and the air temperature is known, it is possible to calculate the amount of noise in each image pixel. From this a variable threshold can be created that is higher in the areas having a small temperature difference and lower where the difference is large.

Even after the variable threshold is applied there can still be noise left in the image. This noise can be modeled as salt-and-pepper noise and can be removed by a median filter. Salt-and-pepper noise is noise that is set to the extreme values having pixel values equal to zero or to the maximum value. Since the median filter also may distort the shape of the gas jet it is preferably only used to achieve a mask. This mask is used to remove all noise outside the gas jet.

Since it is the large gas jet that is of interest some morphological operations are performed on this mask to remove small structures and enlarge and connect the main jet structure. These can be some erosions and dilations of the mask. After this the mask is applied to the image to achieve only the jet. Since it is not known exactly how much the gas jet has spread, this mask should be dilated a little extra.

It is not known how much of the small structures in the image are noise and how much are turbulence. But since the smallest turbulent structures have the shortest lifetime they are least likely to survive between two frames in the video sequence. This makes these structures less interesting for two reasons. Before any further calculations are performed they are removed. This is done by a Gaussian filter that smoothes the images. A Gaussian filter has the property that the total amount of gas in the image remains constant.

If statistically properties of the signal are known, a Wiener filter can also be used in order to filter the images.

Further, embodiments of the invention can also comprise post filtering, i.e. filtering of the image after the point source has been located. Post filtering may be desirable. If there for instance are hundreds of correctly classified leaks and less than ten erroneous one, then the odd leaks can be removed. In the same way, if a leak is not found in a few frames but found in many frames before and after, the leak can be assumed to exist in these frames as well. After running such filters a sequence can be obtained with the source of the leak correctly classified in all frames but the very first ones as described above. These kinds of filters can not be used in a real time application though.

It should be understood, that the described method works for many different sizes of the gas leak. Some definitions may however be changed in order to handle different leak sizes. For example, the number of pixels between two structures in order to consider the structures as close may be varied. Further, one way to make it work as it is for different sizes are to search in a Gaussian pyramid.

Since all or many of the steps and calculations described above can be done in a computer using a digital video sequence all calculations have to be performed in the discrete domain. This can be done by replacing all the integrals with summations and all the continuous functions with sampled versions.

The present invention further relates to an equipment for automated localization of a point source of a visualized gas leak. Said equipment comprises or is connectable to means that utilizes a gas visualization technique and performs the described steps for localization of a point source of a visualized gas leak, cf. FIGS. 5–8. Reference is also made to the applicant's applications WO 01/48459 and EP 1 257 807.

Figure 5:
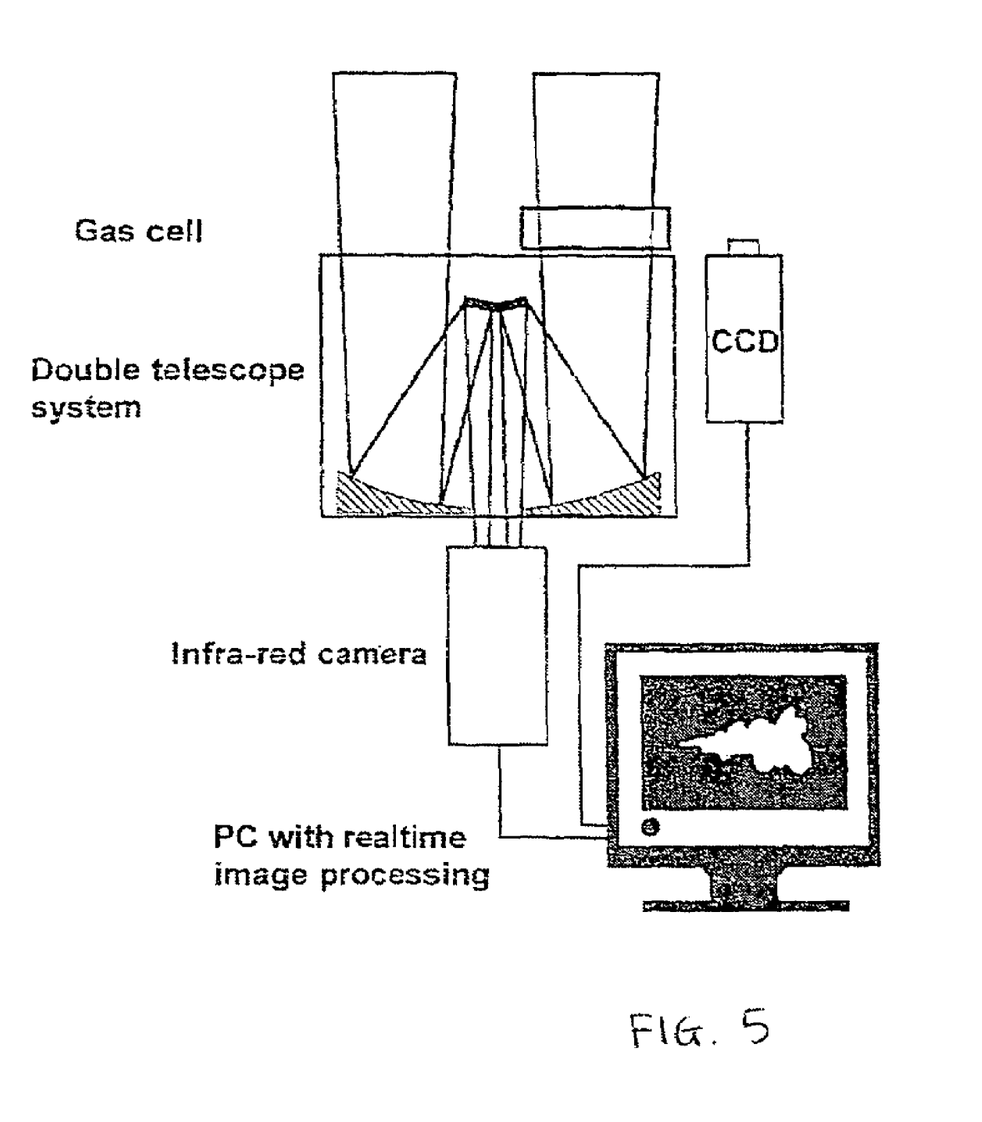
FIG. 5 shows an embodiment of an equipment for locating the point source utilizing the gas correlation technique with a double telescope system.

FIG. 5 shows an embodiment of an equipment for locating the point source utilizing the gas correlation technique with a double telescope system. Emanating gas from a plant is monitored with a double telescope system, where one optical channel passes a gas correlation cell and where the two images are placed side by side in the image plane of a sensitive infrared camera.

Figure 6:
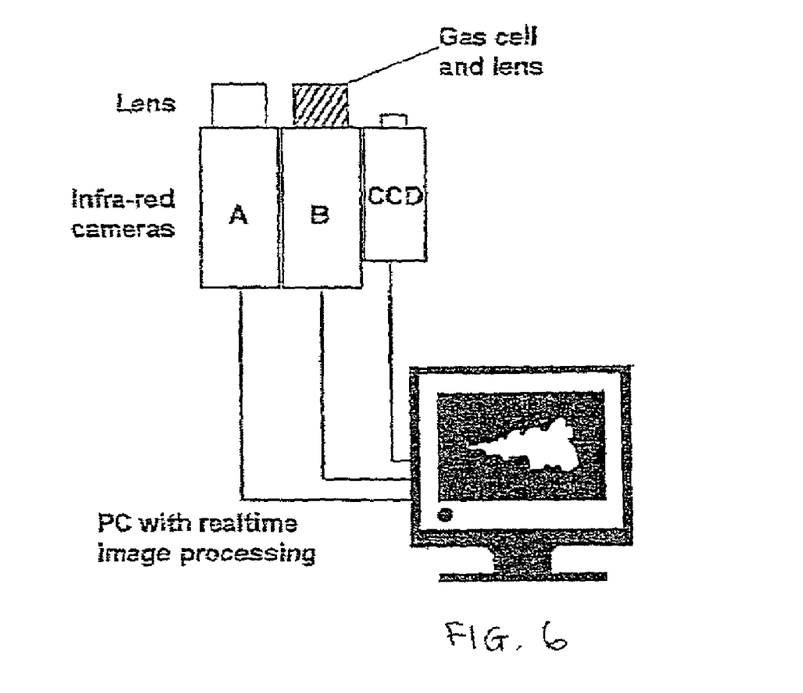
FIG. 6 shows an embodiment of an equipment for locating the point source utilizing the gas correlation technique with two infra-red cameras with the gas cell and lens mounted together on one of the cameras.
Figure 7:
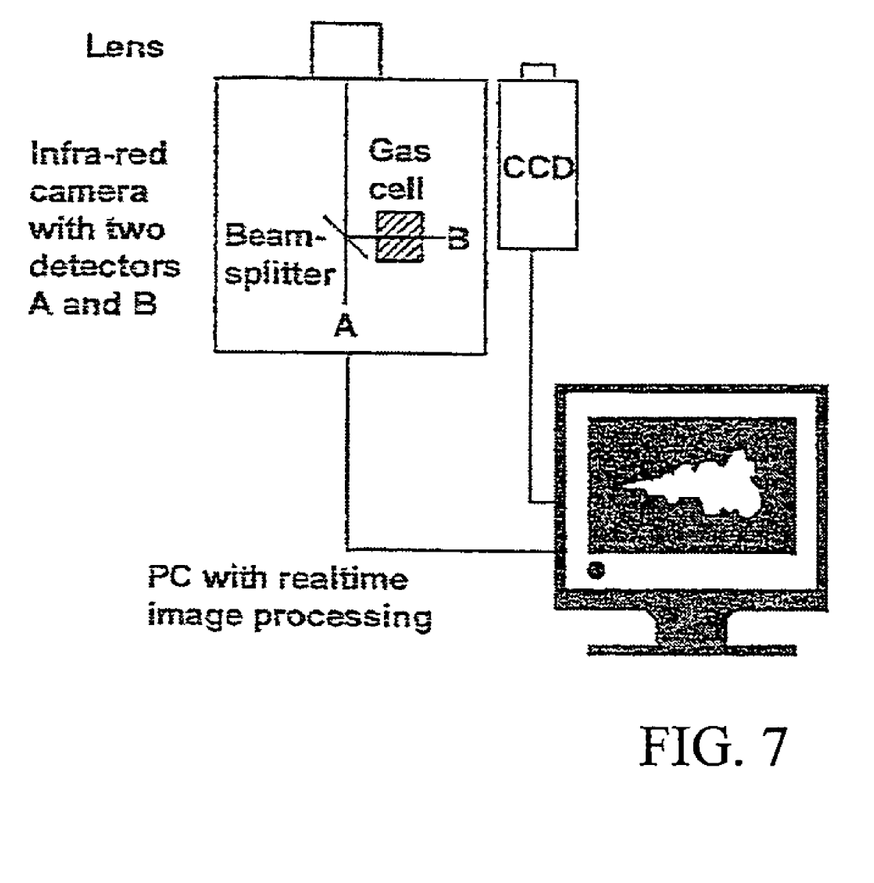
FIG. 7 shows an embodiment of an equipment for locating the point source utilizing the gas correlation technique with a beamsplitter inside the infra-red camera. The gas cell is situated in front of detector B.
Figure 8:
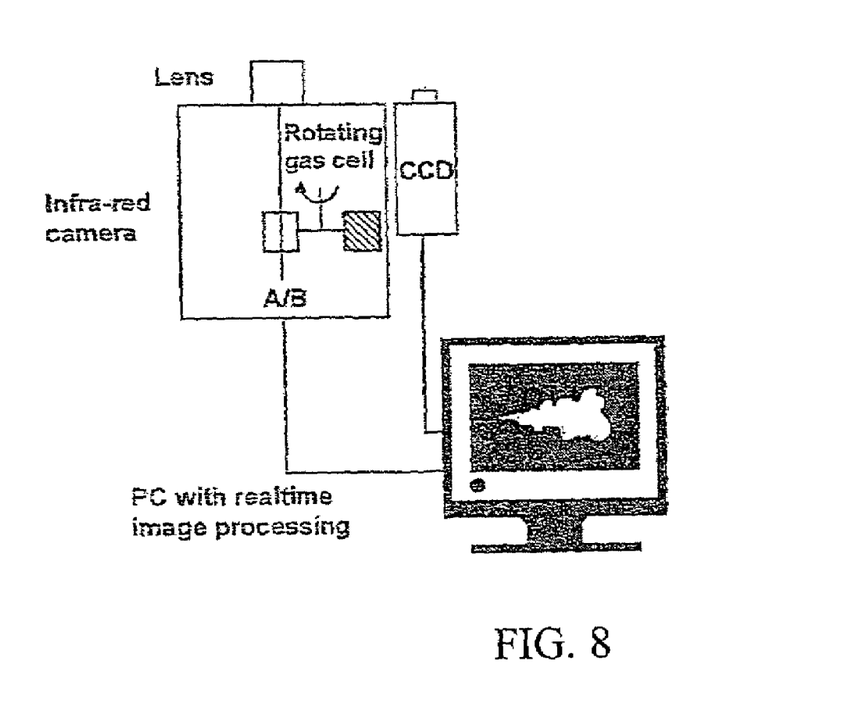
FIG. 8 shows an embodiment of an equipment for locating the point source utilizing the gas correlation technique with a rotating chopper mounted gas cell inside the infra-red camera. The images are sequentially captured by a single detector.

Alternatively, the two images A and B can be produced by two infra-red cameras mounted together, as shown in FIG. 6, or with a single camera with a beamsplitting unit and a gas correlation cell in front of one of two detectors inside the camera as seen in FIG. 7. Another solution is to use a single detector camera with the gas correlation cell mounted on a chopper in front of the detector, for sequential capturing of the images A and B, as shown in FIG. 8.

The present invention refers also to a monitoring system (not shown) comprising or connectable to the equipment for localization of the point source of a visualized gas leak. Such a monitoring system can for example be a monitoring system of a refinery or a plant. The monitoring system also comprises means that provide information to e.g. an operator regarding which component or subsystem of a plant that has a gas leak, thereby improving and simplifying the decision-making for an operator. Since the operator receives information about the location of the source of gas leak in relation to the physical construction of the plant it will be easy for the operator to take appropriate care of the gas leak, e.g. to decide whether to shut down a subsystem of the plant in order to replace or repair a component of the subsystem or to shut down the entire plant.

However, the monitoring system can comprise means that provide gas leak information that is to be analyzed, preferably automatically, by means of a computerized device connected to or comprised in the monitoring system. The computerized device can further be configured to control the operation of the refinery or the plant in dependence of the result of the analysis. That is, the computerized device can be configured to automatically shut down the plant or a part of the plant if a gas leak is detected.

Though the invention has been described with reference to gas absorption images, it should be understood that the invention also can be applied to gas concentration images as well, since the two types of images are strongly connected.

The invention claimed is:

1. A method for automated localization of a point source of a visualized gas leak, comprising the steps of searching in a corner response function $crf(x^*,y^*,\tau)$, said corner response function $crf(x^*,y^*,\tau)$ being calculated based on a number of frames of said gas leak, for maximum values in the $(x^*,y^*)$ variables that are stable over the time variable $\tau$ and considering a point $(x^*,y^*)$ as said point source if said corner response function $crf(x^*,y^*,\tau)$ has a maximum value in said point $(x^*,y^*)$ and said point $(x^*,y^*)$ is temporally stable.

2. A method for automated localization of a point source of a visualized gas leak, comprising the steps of:
    taking a number of frames of said gas leak, said frames being separated in time;
    calculating a corner response function (crf) based on said number of frames;
    determining one or several local maximum points of said corner response function (crf) and considering said local maximum points as possible sources of leakage;
    determining whether said possible sources are temporally stable; and
    considering one or several of said possible sources which is temporally stable as said point source of said visualized gas leak.

3. The method of claim 1, further comprising the steps of calculating a temporal average $f(x,y,\tau)$ of said number of frames of said gas leak before calculating said corner response function and calculating said corner response function of said temporal average.

4. The method of claim 3, wherein the temporal average $f(x,y,\tau)$ is calculated as $$f(x, y, \tau) = \frac{1}{t_0} \int_{\tau-t_0}^{\tau} g(x, y, t) \partial t,$$

where g(x,y,t) is the three-dimensional projection of the four-dimensional function of the gas distribution in time and space, whereby the spatial areas far from the source with a lot of turbulence will be smoothed.

5. The method of claim 4, wherein the corner response function (crf) is calculated in the spatial directions, by evaluating the singular covariance matrices of the spatial gradient of $f(x,y,\tau)$, wherein the matrix is defined as m=aa* where a is defined as $$a = \begin{pmatrix} \frac{\partial f}{\partial x} \\ \frac{\partial f}{\partial y} \end{pmatrix};$$

calculating the spatial average of $m(x,y,\tau)$ as $$m^*(x^*, y^*, \tau) = \int_{x,y \in N(x^*,y^*)} m(x, y, \tau) \partial x \partial y$$

where $N(x^*,y^*)$ is a small area around the point $(x,y^*)$;
    calculating the eigenvalues $(\lambda_1(x^*,y^*,\tau),\lambda_2(x^*,y^*,\tau))$ of $m^*(x^*,y^*,\tau)$;
    determining the corner response function (crf) as $crf(x^*,y^*,\tau)=c|\lambda_1\lambda_2|-|\lambda_1^2+\lambda_2^2|$ where c is a constant, whereby the corner response function $crf(x^*,y^*,\tau)$ will be large in areas where the temporal average $f(x,y,\tau)$ has a large gradient that is changing a lot.

6. The method of claim 5, further comprising the step of weighting the spatial average by a factor depending on the distance from the point $(x^*,y^*)$.

7. The method of claim 6, further comprising the steps of:
    calculating all the spatial local maximum points of $crf(x^*,y^*,\tau)$ for each value of $\tau$;

finding the point ($x_{max}^*, y_{max}^*$) with the largest value of crƒ($x^*, y^*, \tau$) for each time $\tau$;

using a threshold value based on the found largest value crƒ($x^*, y^*, \tau$) to remove points having a corner response value less than k·crƒ($x_{max}^*, y_{max}^*, \tau$), where k is a constant between 0 and 1.

8. The method of claim 3, wherein the corner response function (crf) is calculated in the spatial directions, by evaluating the singular covariance matrices of the spatial gradient of ƒ($x, y, \tau$), wherein the matrix is defined as m=aa* where a is defined as $$a = \begin{pmatrix} \frac{\partial f}{\partial x} \\ \frac{\partial f}{\partial y} \end{pmatrix};$$

calculating the spatial average of m($x, y, \tau$) as $$m^*(x^*, y^*, \tau) = \iint_{x,y \in N(x^*, y^*)} m(x, y, \tau) \partial x \partial y$$

where N($x^*, y^*$) is a small area around the point ($x^*, y^*$);

calculating the eigenvalues ($\lambda_1(x^*, y^*, \tau), \lambda_2(x^*, y^*, \tau)$) of m*($x^*, y^*, \tau$);

determining the corner response function (crf) as crƒ($x^*, y^*, \tau$)=c |$\lambda_1\lambda_2$|−|$\lambda_1^2 + \lambda_2^2$| where c is a constant, whereby the corner response function crƒ($x^*, y^*, \tau$) will be large in areas where the temporal average ƒ($x, y, \tau$) has a large gradient that is changing a lot.

9. The method of claim 8, further comprising the step of weighting the spatial average by a factor depending on the distance from the point ($x^*, y^*$).

10. The method of claim 8, further comprising the steps of calculating all the spatial local maximum points of crƒ ($x^*, y^*, \tau$) for each value of $\tau$;

finding the point ($x_{max}^*, y_{max}^*$) with the largest value of crƒ($x^*, y^*, \tau$) for each time $\tau$;

using a threshold value based on the found largest value crƒ($x^*, y^*, \tau$) to remove points having a corner response value less than k·cr ƒ($x_{max}^*, y_{max}^*, \tau$), where k is a constant between 0 and 1.

11. The method of claim 8, further comprising the steps of:

determining how a point ($x_t^*, y_t^*$) alter with the $\tau$ variable;

determining a point ($x_t^*, y_t^*$) as stable in the $\tau$ variable at the time $\tau_1$ if there exist at least one point in every set between [$\tau_1 - \Delta\tau, \tau_1$] that belong to the open ball $B_r$ ($x_1^*, y_1^*$), where r is a constant distance, measured with some norm.

12. The method of claim 9, further comprising the steps of:

calculating all the spatial local maximum points of crƒ ($x^*, y^*, \tau$) for each value of $\tau$;

finding the point ($x_{max}^*, y_{max}^*$) with the largest value of crƒ($x^*, y^*, \tau$) for each time $\tau$;

using a threshold value based on the found largest value crƒ($x^*, y^*, \tau$) to remove points having a corner response value less than k·crƒ($x_{max}^*, y_{max}^*, \tau$), where k is a constant between 0 and 1.

13. The method of claim 9, further comprising the steps of:

determining how a point ($x_t^*, y_t^*$) alter with the $\tau$ variable;

determining a point ($x_t^*, y_t^*$) as stable in the $\tau$ variable at the time $\tau_1$ if there exist at least one point in every set between [$\tau_1 - \Delta\tau, \tau_1$] that belong to the open ball $B_r$ ($x_1^*, y_1^*$), where r is a constant distance, measured with some norm.

14. The method of claim 5, further comprising the steps of:

calculating all the spatial local maximum points of crƒ ($x^*, y^*, \tau$), for each value of $\tau$;

finding the point ($x_{max}^*, y_{max}^*$) with the largest value of crƒ($x^*, y^*, \tau$) for each time $\tau$;

using a threshold value based on the found largest value crƒ($x^*, y^*, \tau$), to remove points having a corner response value less than k·crƒ($x_{max}^*, y_{max}^*, \tau$), where k is a constant between 0 and 1.

15. The method of claim 5, further comprising the steps of:

determining how a point ($x_t^*, y_t^*$) alter with the $\tau$ variable;

determining a point ($x_t^*, y_t^*$) as stable in the $\tau$ variable at the time $\tau_1$ if there exist at least one point in every set between [$\tau_1 - \Delta\tau, \tau_1$] that belong to the open ball $B_r$ ($x_1^*, y_1^*$), where r is a constant distance, measured with some norm.

16. The method of claim 6, further comprising the steps of:

determining how a point ($x_t^*, y_t^*$) alter with the $\tau$ variable;

determining a point ($x_t^*, y_t^*$) as stable in the $\tau$ variable at the time $\tau_1$ if there exist at least one point in every set between [$\tau_1 - \Delta\tau, \tau_1$] that belong to the open ball $B_r$ ($x_1^*, y_1^*$), where r is a constant distance, measured with some norm.

17. The method of claim 1, wherein said number of frames of said gas leak is a number of gas concentration images or gas absorption images.

18. The method of claim 1, further comprising the step of reducing the noise in said number of frames of the gas leak, said noise reduction being performed prior and/or after said localization of said point source.

19. Equipment for automated localization of a point source of a visualized gas leak, said equipment utilizing a gas visualization technique and comprising means for performing the steps according to claim 1.

20. A monitoring system for automated localization of a point source of a visualized gas leak, said monitoring system comprising an equipment utilizing a gas visualization technique, means for performing the steps according to claim 1, and is configured to provide information relating to a component or subsystem of a plant, which component or subsystem has a gas leak.

21. The monitoring system of claim 20, characterized in that a computerized device is connected to or comprised in said monitoring system and configured to analyze said information and to control the operation of said subsystem or plant in dependence of the result of the analysis of said information.

22. A computer program product for automated localization of a point source of a visualized gas leak, said computer program product comprising means for carrying out the steps and functions of claim 1 when run on a computerized system.

23. The method of claim 12, further comprising the steps of calculating a temporal average ƒ($x, y, \tau$) of said number of frames of said gas leak before calculating said corner response function and calculating said corner response function of said temporal average.

24. The method of claim 23, wherein the temporal average $f(x,y,\tau)$ is calculated as $$f(x, y, \tau) = \frac{1}{t_0} \int_{\tau-t_0}^{\tau} g(x, y, t)\partial t,$$

where $g(x,y,t)$ is the three-dimensional projection of the four-dimensional function of the gas distribution in time and space, whereby the spatial areas far from the source with a lot of turbulence will be smoothed.

25. The method of claim 24, wherein the corner response function (crf) is calculated in the spatial directions, by evaluating the singular covariance matrices of the spatial gradient of $f(x,y,\tau)$, wherein the matrix is defined as $m=aa^*$ where a is defined as $$a = \begin{pmatrix} \partial f/\partial x \\ \partial f/\partial y \end{pmatrix};$$

calculating the spatial average of $m(x,y,\tau)$ as $$m^*(x^*, y^*, \tau) = \int_{x,y \in N} \int_{(x^*,y^*)} m(x, y, \tau)\partial x \partial y$$

where $N(x^*,y^*)$ is a small area around the point $(x^*,y^*)$;
calculating the eigenvalues $(\lambda_1(x^*,y^*,\tau),\lambda_2(x^*,y^*,\tau))$ of $m^*(x^*,y^*,\tau)$;
determining the corner response function (crf) as crf($x^*$, $y^*$,$\tau$)=c$|\lambda_1\lambda_2|-|\lambda_1^2+\lambda_2^2|$ where c is a constant, whereby the corner response function crf($x^*,y^*,\tau$) will be large in areas where the temporal average $f(x,y,\tau)$ has a large gradient that is changing a lot.

26. The method of claim 25, further comprising the step of weighting the spatial average by a factor depending on the distance from the point $(x^*,y^*)$.

27. The method of claim 26, further comprising the steps of:
calculating all the spatial local maximum points of crf $(x^*,y^*,\tau)$ for each value of $\tau$;
finding the point $(x_{max}^*,y_{max}^*)$ with the largest value of crf($x^*,y^*,\tau$) for each time $\tau$;
using a threshold value based on the found largest value crf($x^*,y^*,\tau$) to remove points having a corner response value less than k·cff($x_{max}^*,y_{max}^*,\tau$), where k is a constant between 0 and 1.

28. The method of claim 23, wherein the corner response function (crf) is calculated in the spatial directions, by evaluating the singular covariance matrices of the spatial gradient of $f(x,y,\tau)$, wherein the matrix is defined as $m=aa^*$ where a is defined as $$a = \begin{pmatrix} \dfrac{\partial f}{\partial x} \\ \dfrac{\partial f}{\partial y} \end{pmatrix};$$

calculating the spatial average of $m(x,y,\tau)$ as $$m^*(x^*, y^*, \tau) = \int\int_{x,y \in N(x^*,y^*)} m(x, y, \tau)\partial x \partial y$$

where $N(x^*,y^*)$ is a small area around the point $(x^*,y^*)$;
calculating the eigenvalues $(\lambda_1(x^*,y^*,\tau),\lambda_2(x^*,y^*,\mathbf{96}))$ of $m^*(x^*,y^*,\tau)$:
determining the corner response function (crf) as crf($x^*$, $y^*$,$\tau$)=$|\lambda_1\lambda_2|-|\lambda_1^2+\lambda_2^2|$ where c is a constant, whereby the corner response function cff($x^*,y^*,\tau$) will be large in areas where the temporal average $f(x,y,\tau)$ has a large gradient that is changing a lot.

29. The method of claim 28, further comprising the step of weighting the spatial average by a factor depending on the distance from the point $(x^*,y^*)$.

30. The method of claim 28, further comprising the steps of:
calculating all the spatial local maximum points of crf $(x^*,y^*,\tau)$ for each value of $\tau$;
finding the point $(x_{max}^*,y_{max}^*)$ with the largest value of crf($x^*,y^*,\tau$) for each time $\tau$;
using a threshold value based on the found largest value crf($x^*,y^*,\tau$) to remove points having a corner response value less than k·crf($x_{max}^*,y_{max}^*,\tau$), where k is a constant between 0 and 1.

31. The method of claim 28, further comprising the steps of:
determining how a point $(x_t^*,y_t^*)$ alter with the $\tau$ variable;
determining a point $(x_t^*,y_t^*)$ as stable in the $\tau$ variable at the time $\tau_1$ if there exist at least one point in every set between $[\tau_1-\Delta\tau,\tau_1]$ that belong to the open ball $B_r$ $(x_1^*,y_1^*)$, where r is a constant distance, measured with some norm.

32. The method of claim 29, further comprising the steps of:
calculating all the spatial local maximum points of crf $(x^*,y^*,\tau)$ for each value of $\tau$;
finding the point $(x_{max}^*,y_{max}^*)$ with the largest value of crf($x^*,y^*,\tau$) for each time $\tau$;
using a threshold value based on the found largest value crf($x^*,y^*,\tau$) to remove points having a corner response value less than k·crf($x_{max}^*,y_{max}^*,\tau$) where k is a constant between 0 and 1.

33. The method of claim 29, further comprising the steps of:
determining how a point $(x_t^*,y_t^*)$ alter with the $\tau$ variable;
determining a point $(x_t^*,y_t^*)$ as stable in the $\tau$ variable at the time $\tau_1$ if there exist at least one point in every set between $[\tau_1-\Delta\tau,\tau_1]$ that belong to the open ball $B_r$ $(x_1^*,y_1^*)$, where r is a constant distance, measured with some norm.

34. The method of claim 25, further comprising the steps of:
calculating all the spatial local maximum points of crf $(x^*,y^*,\tau)$ for each value of $\tau$;
finding the point $(x_{max}^*,y_{max}^*)$ with the largest value of crf($x^*,y^*,\tau$) for each time $\tau$;
using a threshold value based on the found largest value crf($x^*,y^*,\tau$) to remove points having a corner response value less than k·crf($x_{max}^*,y_{max}^*,\tau$), where k is a constant between 0 and 1.

35. The method of claim 25, further comprising the steps of
   determining how a point $(x_t^*,y_t^*)$ alter with the $\tau$ variable;
   determining a point $(x_t^*,y_t^*)$ as stable in the $\tau$ variable at the time $\tau_1$ if there exist at least one point in every set between $[\tau_1-\Delta\tau,\tau_1]$ that belong to the open ball $B_r(x_1^*,y_1^*)$, where r is a constant distance, measured with some norm.

36. The method of claim 26, further comprising the steps of:
   determining how a point $(x_t^*,y_t^*)$ alter with the $\tau$ variable;
   determining a point $(x_t^*,y_t^*)$ as stable in the $\tau$ variable at the time $\tau_1$ if there exist at least one point in every set between $[\tau_1-\Delta\tau,\tau_1]$ that belong to the open ball $B_r(x_1^*,y_1^*)$, where r is a constant distance, measured with some norm.

37. The method of claim 2, wherein said number of frames of said gas leak is a number of gas concentration images or gas absorption images.

38. The method of claim 2, further comprising the step of reducing the noise in said number of frames of the gas leak, said noise reduction being performed prior and/or after said localization of said point source.

39. Equipment for automated localization of a point source of a visualized gas leak, said equipment utilizing a gas visualization technique and comprising means for performing the steps according to claim 1.

40. A monitoring system for automated localization of a point source of a visualized gas leak, said monitoring system comprising an equipment utilizing a gas visualization technique, means for performing the steps according to claim 2, and is configured to provide information relating to a component or subsystem of a plant, which component or subsystem has a gas leak.

41. The monitoring system of claim 40, characterized in that a computerized device is connected to or comprised in said monitoring system and configured to analyze said information and to control the operation of said subsystem or plant in dependence of the result of the analysis of said information.

42. A computer program product for automated localization of a point source of a visualized gas leak, said computer program product comprising means for carrying out the steps and functions of claim 2 when run on a computerized system.

* * * * *